(12) United States Patent
Suzuki et al.

(10) Patent No.: US 6,478,940 B1
(45) Date of Patent: Nov. 12, 2002

(54) GAS CONCENTRATION SENSING APPARATUS CAPABLE OF SUPPRESSING SENSOR VOLTAGE OSCILLATION

(75) Inventors: Toshiyuki Suzuki, Handa (JP); Eiichi Kurokawa, Okazaki (JP); Satoshi Hada, Kariya (JP); Tomoo Kawase, Nagoya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/383,383

(22) Filed: Aug. 26, 1999

(30) Foreign Application Priority Data

Sep. 4, 1998 (JP) ............................................ 10-251285

(51) Int. Cl.$^7$ ............................................... G01N 27/41
(52) U.S. Cl. ........................ 204/425; 204/426; 204/406
(58) Field of Search ................................ 204/406, 424, 204/425, 426, 408; 73/23.32

(56) References Cited

U.S. PATENT DOCUMENTS

| | | | |
|---|---|---|---|
| 4,407,704 A | * 10/1983 | Mase et al. | 204/406 |
| 4,664,773 A | 5/1987 | Suzuki et al. | 204/406 |
| 4,718,999 A | * 1/1988 | Suzuki et al. | 204/406 |
| 4,767,520 A | * 8/1988 | Asakura et al. | 204/406 |
| 4,818,362 A | * 4/1989 | Asakura et al. | 204/406 |
| 4,877,511 A | * 10/1989 | Nakajima et al. | 204/406 |
| 4,882,030 A | 11/1989 | Suzuki et al. | 204/406 |
| 5,405,521 A | * 4/1995 | Nakamori et al. | 204/425 |
| 6,084,418 A | * 7/2000 | Takami et al. | 324/717 |

FOREIGN PATENT DOCUMENTS

| | | |
|---|---|---|
| EP | 816 836 | 1/1998 |
| JP | 7-18837 | 3/1995 |
| JP | 2509905 | 4/1996 |
| JP | 10-19842 | 1/1998 |

OTHER PUBLICATIONS

Barnaal, "Analog Electronics for Scientific Application", pp. A208–209, 1982, month unknown.*

* cited by examiner

*Primary Examiner*—Robert J. Warden, Sr.
*Assistant Examiner*—Kaj K. Olsen
(74) *Attorney, Agent, or Firm*—Nixon & Vanderhye P.C.

(57) ABSTRACT

A limit-current type A/F sensor produces element current responsive to oxygen concentration in the exhaust gas when a voltage is applied to its sensor element portion. An application voltage control circuit comprises an operational amplifier and resistors. An output of the control circuit is applied to one terminal of the A/F sensor via a driver circuit. The other terminal of the A/F sensor is connected to an output terminal of an operational amplifier via a current-detecting resistor. The element current value, detected by the current-detecting resistor, is returned to the application voltage control circuit via a buffer. In the application voltage control circuit, adjustment of the gain is performed in such a manner that the inclination of the application voltage line on the V-I coordinate becomes larger than the inclination equivalent to the A.C. impedance of the sensor element in the sensor activated condition.

15 Claims, 14 Drawing Sheets

APPLICATION VOLTAGE

ELEMENT CURRENT

INTER-TERMINAL RESISTANCE

GAS CONCENTRATION SENSING APPARATUS CAPABLE OF SUPPRESSING SENSOR VOLTAGE OSCILLATION

BACKGROUND OF THE INVENTION

The present invention relates to a gas concentration sensing apparatus using a gas concentration sensor which detects a concentration of a specific component of a measured gas, such as oxygen involved in an exhaust gas emitted from an automotive vehicle engine. More specifically, the present invention relates to a gas concentration sensing apparatus which is capable of adequately controlling a voltage applied to the gas concentration sensor.

There are conventional gas concentration sensors each comprising a solid electrolytic element for detecting a specific component of a measured gas. For example, a limit-current type air-fuel ratio sensor (referred to as A/F sensor) detects an oxygen concentration in an exhaust gas. The A/F sensor produces a current signal responsive to the oxygen concentration in the exhaust gas (i.e., air-fuel ratio), when a voltage is applied to the sensor element. The solid electrolytic element (i.e., sensor element) of the limit-current type sensor may be zirconia. The A.C. characteristics of this limit-current type sensor is stabile in a high frequency region of the application voltage equal to or higher than 1 kHz. When an element resistance is detected, an application voltage has a frequency determined by considering the A.C. characteristics of the solid electrolytic element. In such detection of the element resistance utilizing the sensor AC characteristics, an A.C. impedance of the element is obtained from a variation amount of the application voltage and a variation amount of a corresponding current.

$$A.C. \text{impedance} = \text{voltage variation/current variation}$$

To accurately detect the air-fuel ratio, it is necessary to adequately control the application voltage. To realize this, the applicant has previously proposed, as one of prospective systems, an "air-fuel ratio detecting apparatus" in the published Japanese patent application No. 10-185861. According to this air-fuel ratio detecting apparatus, the voltage applied to the A/F sensor is controlled by a microcomputer. Especially, a change speed of the application voltage is variably controlled. More specifically, the change rate of the application voltage is small in a specific region corresponding to the stoichiometric A/F value and its vicinity compared with change rates in other regions. Such settings make it possible to improve sensing accuracy in the air-fuel ratio detecting operation.

When the microcomputer is used, the application voltage to the A/F sensor is controlled in the following manner. The microcomputer generates a digital signal representing an application voltage. This digital signal is converted into an analog signal by a D/A converter. The application voltage, thus converted into the analog signal, is applied to the A/F sensor. When the voltage applied to the A/F sensor shows stepwise changes periodically, a tailing phenomenon appears on an element current (i.e., sensor current) at each timing corresponding to each stepwise change of the application voltage as shown in FIG. 16. This tailing phenomenon is inherently derived from the A.C. characteristics of the sensor element, and significantly worsens the sensing accuracy in the air-fuel ratio detecting operation. The tailing phenomenon can be suppressed by reducing a step height in each change of the application voltage. However, to realize this, the D/A converter needs to have higher or improved resolution. The cost will be forcibly increased.

According to this kind of A/F sensor, its activated state and/or deteriorated state can be known by detecting an internal resistance of the solid electrolytic element (i.e., element resistance). The detection of the internal resistance of the solid electrolytic element is generally performed by interrupting the air-fuel ratio detecting operation. However, it is desirable to reduce such a dormant period. Accordingly, the D/A or A/D converter and the microcomputer must have high-speed processing capability. This also leads to cost increase.

As described above, the microcomputer equipped apparatus causes various inconveniences.

SUMMARY OF THE INVENTION

In view of the foregoing problems encountered in the prior art, the present invention has an object to provide a gas concentration sensing apparatus which is capable of effectively suppressing the oscillation of the application voltage and accurately detecting a gas concentration.

In order to accomplish this and other related objects, the present invention provides a first gas concentration sensing apparatus comprising a sensor element including a solid electrolytic member with electrodes provided on opposed surfaces of the solid electrolytic member, a gas concentration sensor for generating a current signal responsive to a concentration of a specific component involved in a measured gas when a voltage is applied between the electrodes of the sensor element, and an application voltage control circuit for feedback controlling the application voltage applied to the gas concentration sensor in response to the current signal, characterized in that a resistance value obtainable from a change rate of the application voltage controlled by the application voltage control circuit in response to the current signal is set to be smaller than an A.C. impedance of the sensor element.

Preferably, an application voltage line is defined on a V-I coordinate for determining the voltage applied to the gas concentration sensor from the application voltage control circuit, and an inclination of the application voltage line is larger than an inclination equivalent to the A.C. impedance of the sensor element in a sensor activated condition.

Furthermore, the present invention provides a second gas concentration sensing apparatus comprising a sensor element including a solid electrolytic member with electrodes provided on opposed surfaces of the solid electrolytic member, a gas concentration sensor for generating a current signal responsive to a concentration of a specific component involved in a measured gas when a voltage is applied between the electrodes of the sensor element, and an application voltage control circuit for feedback controlling the voltage applied to the gas concentration sensor in response to the current signal, characterized in that a change speed of the application voltage is suppressed in a feedback loop of the application voltage control circuit.

Preferably, the change speed of the application voltage produced by the application voltage control circuit is reduced in such a manner that a resistance value obtainable by the application voltage per unit time is smaller than an A.C. impedance of the sensor element.

Preferably, a low-pass filter is provided as a delay means for reducing the change speed of the application voltage controlled by the application voltage control circuit in response to the current signal.

Preferably, an operational amplifier constituting the application voltage control circuit has a slow slew rate so as to serve as a delay means for reducing the change speed of the application voltage controlled by the application voltage control circuit in response to the current signal.

Furthermore, the present invention provides a third gas concentration sensing apparatus comprising a sensor element including a solid electrolytic member with electrodes provided on opposed surfaces of the solid electrolytic member, a gas concentration sensor for generating a current signal responsive to a concentration of a specific component involved in a measured gas when a voltage is applied between the electrodes of the sensor element, and an application voltage control circuit for feedback controlling the application voltage applied to the gas concentration sensor in response to the current signal, characterized in that an overall gain of a feedback loop including the gas concentration sensor and the application voltage control circuit is always equal to or smaller than 1.

In the above-described second and third gas concentration sensing apparatus, it is preferable that an application voltage line is defined on a V-I coordinate for determining the voltage applied to the gas concentration sensor, and an inclination of the application voltage line is equalized to an inclination equivalent to a D.C. resistance of the sensor element of the gas concentration sensor in a sensor activated condition.

In this case, the gas concentration sensing apparatus is preferably incorporated in an air-fuel ratio control system for performing a lean burn control of an internal combustion engine.

In all of the above-described first to third gas concentration sensing apparatus, it is preferable to provide a plurality of application voltage lines different in their inclinations on the V-I coordinate to selectively or continuously use the plurality of application voltage lines in accordance with the temperature of the sensor element.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

To solve the problems inherently caused by a microcomputer-based detecting apparatus, the inventors of the present invention have been researching an air-fuel ratio sensing apparatus capable of controlling the voltage applied to the sensor by using an analog circuit instead of using a microcomputer.

However, the air-fuel ratio sensing apparatus using an analog circuit will encounter with the following problems.

Figure 3:
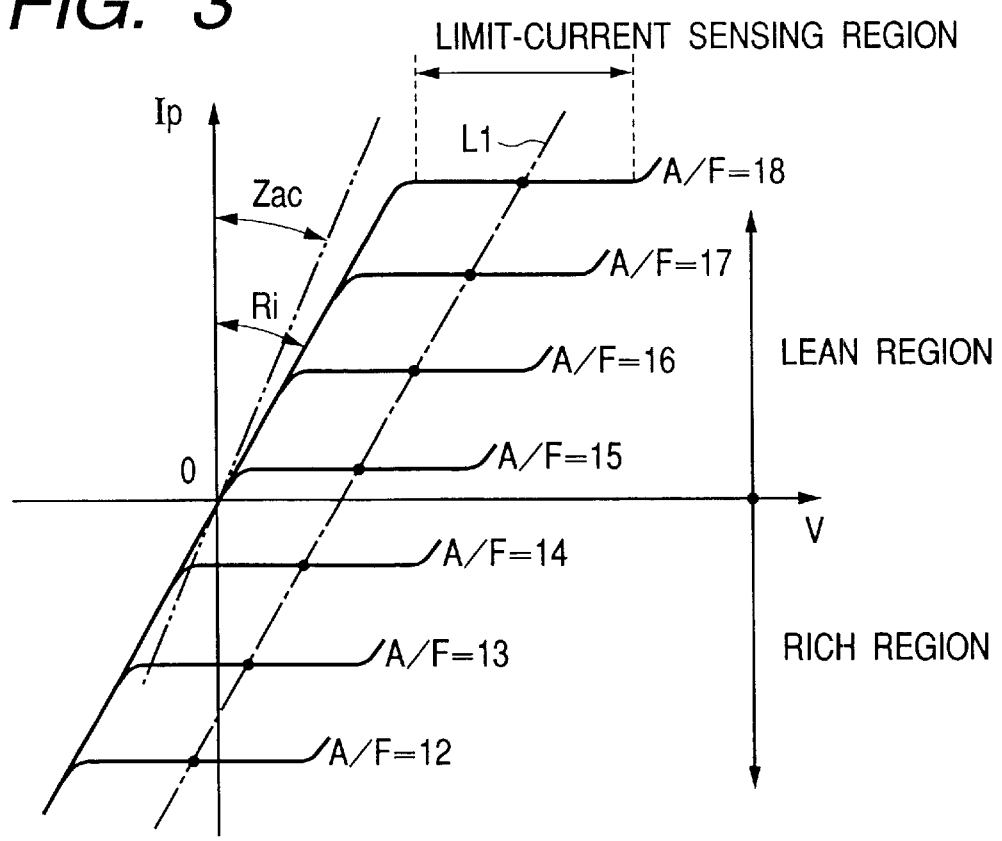
FIG. 3 is a graph showing V-I characteristics of the A/F sensor.

FIG. 3 shows V-I characteristics of a limit-current type sensor. A straight line portion parallel to the V-axis (i.e., the abscissa) of the V-I coordinate corresponds to a limit-current sensing region capable of identifying a limit current flowing across the sensor element (i.e., element current Ip). The change of element current Ip is dependent on increase or decrease of the air-fuel ratio (i.e., the degree of lean or rich). When the air-fuel ratio is in a lean side, the element current Ip shows an increased value. When the air-fuel ratio is in a rich side, the element current Ip shows a decreased value.

On the V-I characteristics, there is a resistance dominant region which extends to a lower voltage side from the straight line portion. The resistance dominant region is expressed by a first-order straight line. The inclination of this first-order straight line is determined by an element D.C. resistance Ri. It is generally known that there is a relationship "Ri>Zac" when Zac represents an A.C. impedance of the sensor element.

An application voltage line L1 is given on the V-I coordinate shown in FIG. 3. This application voltage line L1 is parallel to the first-order straight line representing the resistance dominant region. The application voltage is determined according to this application voltage line L1 with reference to a momentary air-fuel ratio. When the air-fuel ratio is shifted to the lean side, an increased element current Ip flows across the A/F sensor. The application voltage is changed to a larger value in response to the increased element current Ip. Namely, the positive feedback of the application voltage is performed in such a manner that the application voltage increases in response to the increase of the element current Ip. According to such positive feedback control, the application voltage oscillates when the gain of the feedback circuit exceeds "1."

More specifically, when the application voltage shows a steep or quick change due to disturbance or the like, the element current changes abruptly according to the above-described A.C. characteristics. Thus, when the circuit gain exceeds "1", the voltage applied to the A/F sensor becomes larger than an optimum voltage. In this case, the application voltage continuously increases until it reaches an upper limit restricted by the power source voltage. After that, the application voltage starts decreasing. By repeating increase and decrease in this manner, the application voltage causes oscillation. The oscillation of the application voltage gives adverse influence to the sensing accuracy in the air-fuel ratio detecting operation. Furthermore, the A/F sensor is subjected to excessively large voltages for a long time. This will lead to damage of the sensor element.

An "air-fuel ratio sensor" disclosed in Japanese Patent No. 2509905 is a conventional air-fuel ratio sensor. According to this prior art, the voltage applied to the sensor is controlled according to a momentary pump current (i.e., air-fuel ratio) so that the pump current shows stepwise changes each time it reaches the zero point level.

An "air-fuel ratio sensing apparatus" disclosed in Published Japanese Patent Application No. 7-18837 measures an electromotive force produced between first and second electrodes of the sensor. According to this prior art, the voltage applied to the sensor is controlled so as to equalize the electromotive force to a predetermined value.

However, according to each of the above-described prior art apparatuses, no consideration is given to the sensor A.C. characteristics. Therefore, all of these prior art apparatuses will suffer from the undesirable oscillation of the application voltage as described above.

Thus, the present invention has an object to provide a gas concentration sensing apparatus which is capable of effectively suppressing the oscillation of the application voltage and accurately detecting a gas concentration.

To control an application voltage applied to a gas concentration sensor, the application voltage control circuit inputs a detection value of current flowing across the sensor (i.e., a current signal) and varies the application voltage in accordance with the detected current signal. In this case, the circuit performs a positive feedback operation as a whole. Accordingly, when the overall circuit gain exceeds "1", the application voltage oscillates due to the sensor A.C. characteristics.

Figure 13A:
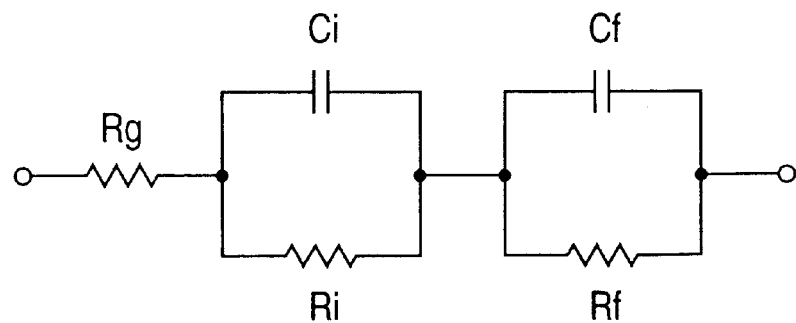
FIG. 13A is a view showing an equivalent circuit of the A/F sensor.
Figure 17:
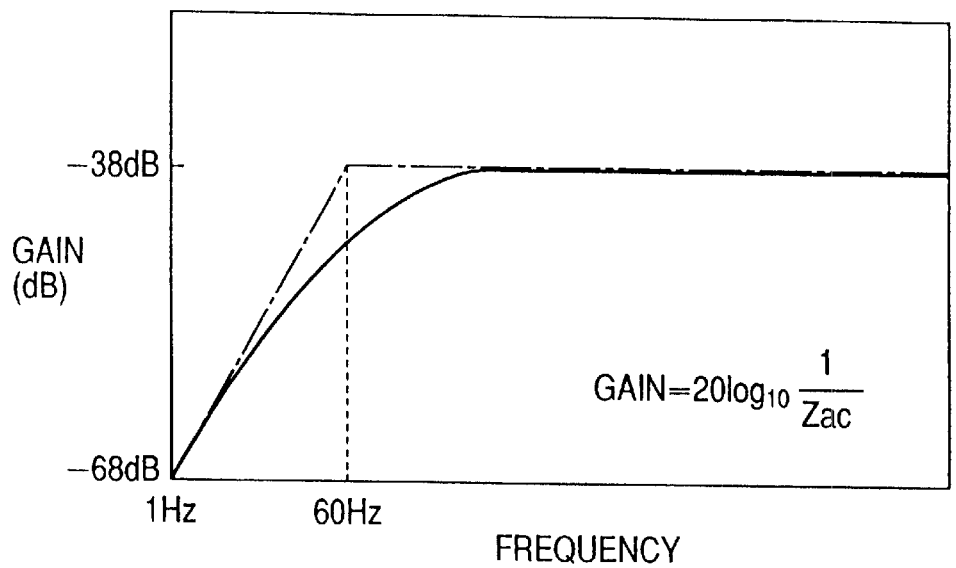
FIG. 17 is a graph showing frequency characteristics of a gas concentration sensor.

This can be explained from the fact that the gas concentration sensor is similar to a high-pass filter (HPF) in the A.C. characteristics as shown in FIG. 17. FIG. 13A is a model showing the gas concentration sensor. As understood from this model, the inter-terminal resistance (i.e., resistance between sensor terminals) decreases with increasing frequency. In FIG. 13A, Rg represents a particle resistance of the solid electrolytic member relative to the oxygen ion. Ri and Ci represent a particle resistance and an intergranular capacitance at a particle surface of the solid electrolytic member, respectively. Rf and Cf represent an electrode surface resistance and an electrode surface capacitance, respectively.

Meanwhile, the gas concentration sensor has an input equal to the application voltage (V) and an output equal to the sensor current (I). Therefore, the gain of this sensor is expressed in the following manner.

Gain=output/input=sensor current($I$)/application voltage($V$)=1/R

In general, the D.C. resistance Ri of the solid electrolytic element is larger than an A.C. impedance Zac of the solid electrolytic element (I.e., Ri>Zac). Accordingly, it is understood that the element A.C. impedance brings a larger gain compared with that of the element D.C. resistance.

Figure 18:
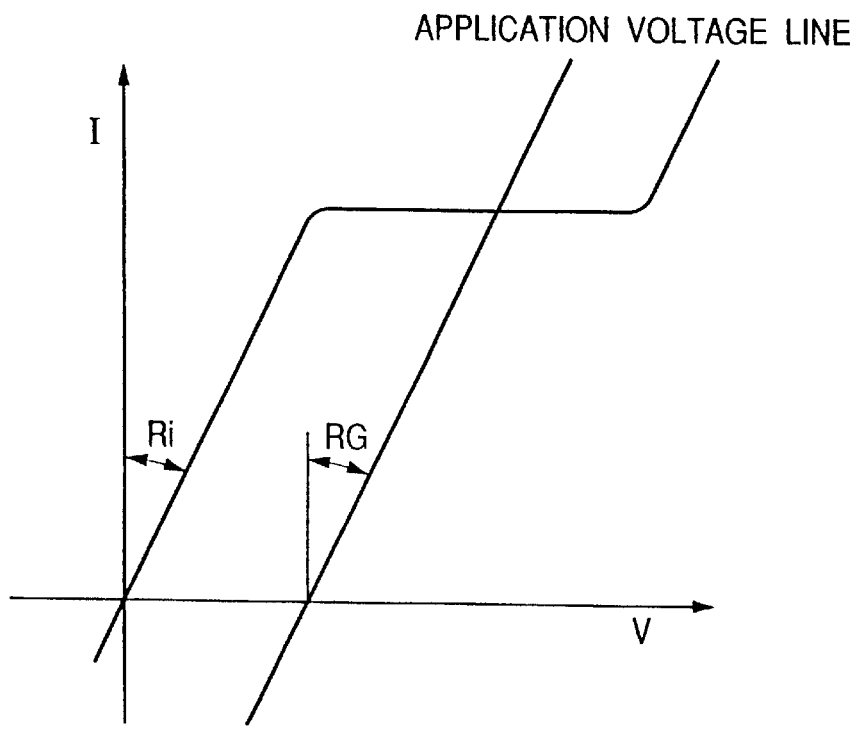
FIG. 18 is a graph showing an application voltage line on a V-I coordinate.

FIG. 18 shows a static V-I characteristics of the gas concentration sensor. It is possible to draw an application voltage line parallel to the element D.C. resistance Ri (i.e., Ri=RG), so that an appropriate voltage is applied to the sensor in response to a variation of a D.C. signal component. However, it is impossible to maintain the application voltage to appropriate values during a transitional state (i.e., against variation of a A.C. signal component). Thus, the application voltage oscillates. In other words, the oscillation is derived from inherent properties of the sensor.

Figure 19:
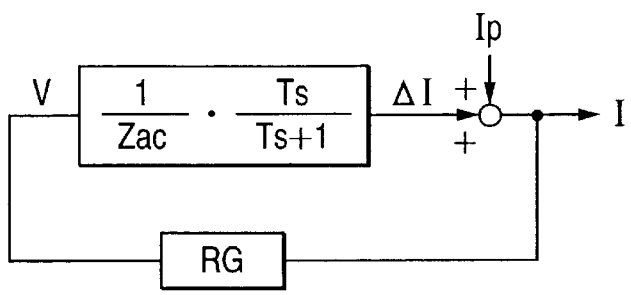
FIG. 19 is a view showing a model of a feedback system.

Hence, it is effective to determine stabilizing condition for preventing the gas concentration sensor from oscillating. In the model shown in FIG. 19, the transfer characteristics of this sensor can be expressed in the following equation.

$$\text{Sensor Transfer Characteristics} = \frac{1}{Zac} \cdot \frac{Ts}{Ts+1} \quad (1)$$

When "RG" represents an inclination of the application voltage line which is determined by the application voltage control circuit and a shunt resistance, the transfer function of this model can be expressed in the following equation.

$$\Delta I = \frac{(RG/Zac) \cdot Ts}{(1 - RG/Zac)Ts + 1} Ip \quad (2)$$

where "T" represents a time constant of the sensor.

Furthermore, a characteristic equation can be expressed in the following manner.

$$s + \frac{1}{T(1 - RG/Zac)} = 0 \quad (3)$$

According to this characteristic equation, the stabilizing condition (i.e., oscillation suppressing condition) can be given in the following manner.

$RG<Zac$

In view of the foregoing, according to the present invention, the application voltage control circuit controls the voltage applied to the sensor in response to the current signal of the sensor. And, a resistance value (i.e., RG=V/I) obtainable from a change rate of the application voltage is set to be smaller than an A.C. impedance (i.e., Zac) of the sensor element. To embody the present invention, an application voltage line is defined on a V-I coordinate for determining the voltage applied to the gas concentration sensor from the application voltage control circuit. And, an inclination of the application voltage line is larger than an inclination equivalent to the A.C. impedance of the sensor element in a sensor activated condition.

Figure 6:
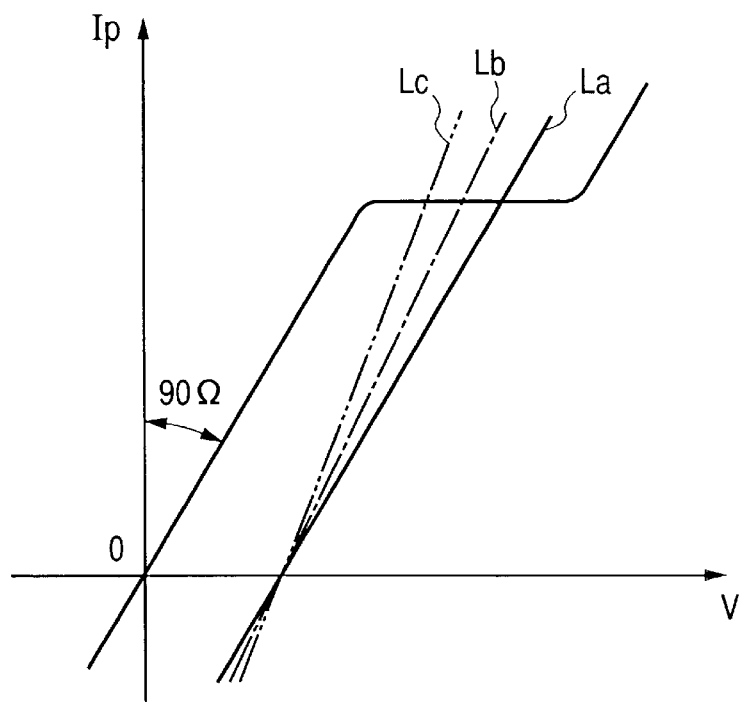
FIG. 6 is a graph showing application voltage lines on a V-I coordinate.

Namely, the application voltage line Lc is given on the V-I coordinate as shown in FIG. 6. A comparative application voltage line La has an inclination equivalent to the element D.C. resistance (i.e., 90Ω) of the sensor. Another comparative application voltage line Lb has an inclination equivalent to the element A.C. impedance of the sensor. The application voltage line Lc is steepest in the inclination angle when it is compared with other application voltage lines La and Lb. The application voltage line Lc is thus used to control the application voltage.

With such settings, it becomes possible to prevent the application voltage from being amplified so excessively that it is brought into oscillated condition, even when the application voltage is changed suddenly due to disturbance such as noises. Hence, it becomes possible to effectively suppress the oscillation of the application voltage. The gas concentration can be accurately detected. Furthermore, the above-described arrangement makes it possible to suppress undesirable oscillation of the application voltage without using a microcomputer which is generally expensive. Using no microcomputer is effective to eliminate the tailing phenomenon caused in response to each change of the application voltage.

The A.C. impedance of the sensor element decreases with increasing element temperature. Thus, the application voltage tends to oscillate when the element temperature is high. Hence, it is preferable to determine the inclination of the application voltage line with reference to the A.C. impedance at a reachable maximum temperature of the sensor element so that the oscillation of the application voltage can be surely suppressed even at this maximum temperature.

Preferably, a change speed of the application voltage is suppressed when the application voltage is controlled by the application voltage control circuit in response to the current signal. In this case, the oscillation phenomenon can be effectively suppressed even when the application voltage is changed suddenly due to disturbance such as noises. Hence, it becomes possible to effectively prevent the oscillation of the application voltage. The gas concentration can be accurately detected.

In a practical arrangement for embodying the invention, it is preferable to reduce the change speed of the application voltage produced by the application voltage control circuit in such a manner that a resistance value obtainable by the application voltage per unit time is smaller than the A.C. impedance of the sensor element.

Figure 20A:
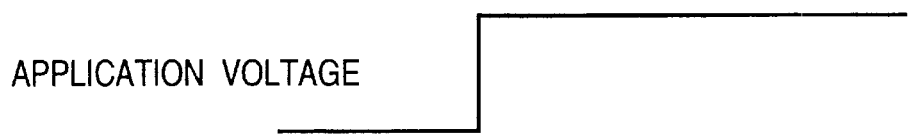
FIG. 20A is a time chart showing the application voltage.
Figure 20B:
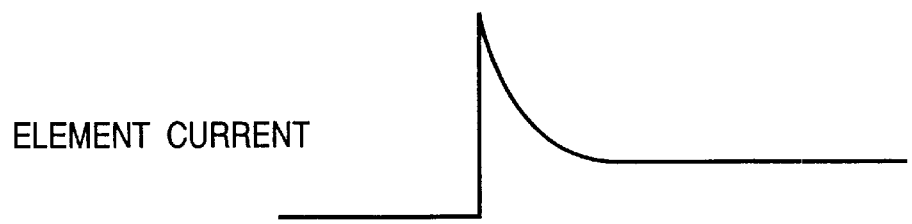
FIG. 20B is a time chart showing the element current.
Figure 20C:
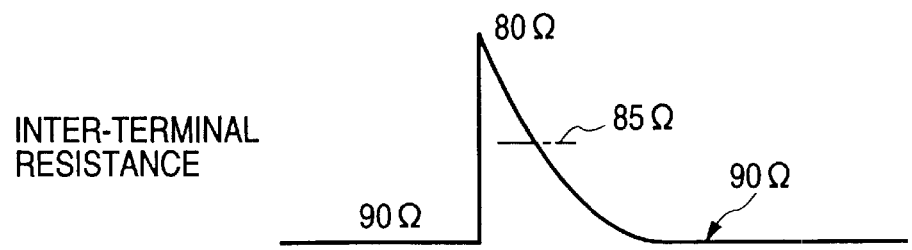
FIG. 20C is a time chart showing the inter-terminal resistance.

In short, when the application voltage changes stepwise as shown in FIG. 20A, the current signal (i.e., the element current) changes as shown in FIG. 20B. When the application voltage changes suddenly, a voltage change per unit time is large. Namely, the frequency component is high. From the A.C. characteristics of the gas concentration sensor, the element A.C. impedance Zac becomes small. However, the frequency component becomes low after the abrupt change of the application voltage. The element A.C. impedance Zac is gradually increased (refer to the frequency characteristics shown in FIG. 17). Meanwhile, as shown in FIG. 20C, the inter-terminal resistance of the gas concentration sensor shows an apparent change in each unit time.

In this case, to suppress the oscillation of the application voltage, it is preferable to set the resistance value obtainable by the application voltage line per unit time to be smaller than the A.C. impedance of the sensor element. The inclination of the application voltage becomes steep. Practically, it is effective to reduce the change speed of the application voltage. In response to the reduction of the change speed of the application voltage, the resistance value obtainable by the application voltage per unit time is reduced. Thus, the application voltage line can temporarily have a steep inclination.

Figure 21A:
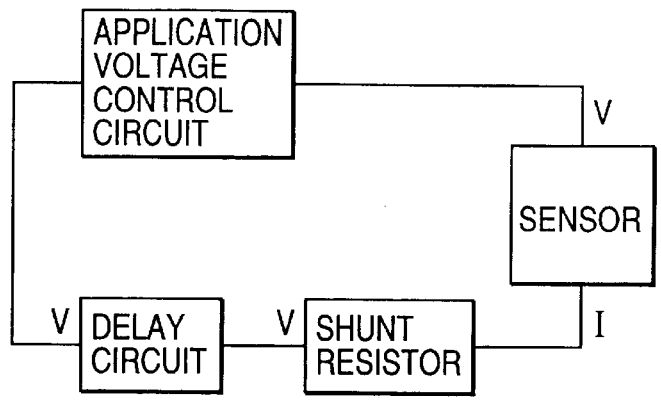
FIG. 21A is a view showing a circuit arrangement of the feedback system.
Figure 21B:
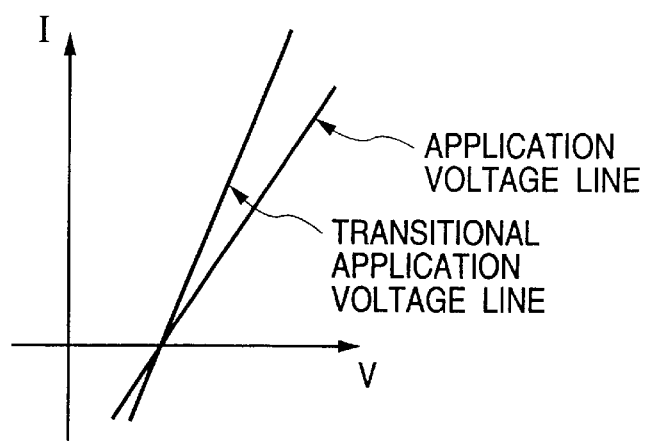
FIG. 21B is a graph showing the V-I characteristics.

For example, the change speed of the application voltage can be suppressed by adding a delay circuit in the feedback system as shown in FIG. 21A. With this arrangement, it becomes possible to suppress a transitional element current (i.e., A.C. current component) which is detectable by a shunt resistance. The application voltage causes a small change in response to a large current change. Thus, the application voltage line has a steep inclination (refer to FIG. 21B). From the foregoing, it becomes possible to suppress the oscillation of the application voltage.

Figure 22:
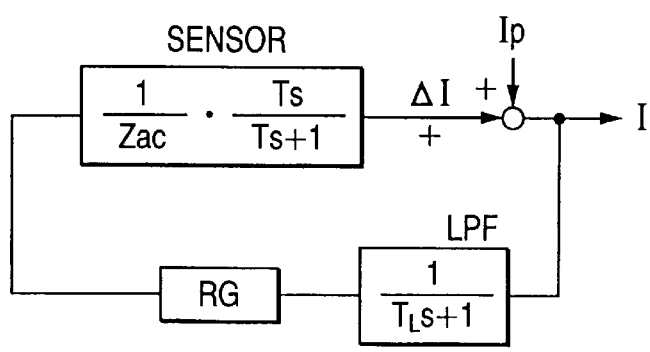
FIG. 22 is a view showing a model of the feedback system.

Preferably, a low-pass filter (i.e., LPF) is provided as a means for delaying the change speed of the application voltage controlled by the application voltage control circuit in response to the current signal. In this case, the LPF moderates or absorbs every prompt voltage change caused by noises or the like. Thus, it becomes possible to eliminate the problems, i.e., the oscillation of the application voltage or deterioration of sensing accuracy in the gas concentration detecting operation. FIG. 22 shows a model including the LPF. The stabilizing condition for suppressing the oscillation can be derived by calculating the transfer function and the characteristic equation in the same manner as in the calculations using the equations 2 and 3. The stabilizing condition in this case can be expressed in the following manner.

$$RG < (1+T_L/T) \cdot Zac$$

where "T" represents the time constant of the sensor, "$T_L$" represents the time constant of the LPF, and "RG" represents the inclination of the application voltage.

Accordingly, adding the LPF enlarges the range of the stabilizing condition and ensures the effect of suppressing the oscillation. Regarding the calculation for the stabilizing condition, the judgement in a narrow sense can be performed by using other judgements, such as Nyquist stability criterion. By adding the LPF, it becomes possible to set an application voltage line parallel to the element D.C. resistance Ri on the V-I characteristics of the sensor element. This eliminates errors in the gas concentration detecting operation.

Preferably, an operational amplifier constituting the application voltage control circuit has a slow slew rate so as to serve as the delay means for reducing the change speed of the application voltage which is controlled by the application voltage control circuit in response to the current signal. For example, the slew rate of this operational amplifier is delayed so that the resistance value obtainable by the application voltage per unit time becomes smaller than the A.C. impedance of the sensor element.

Preferably, an overall gain of a feedback loop including the gas concentration sensor and the application voltage control circuit is always equal to or smaller than 1. It is effective to provide a gas concentration sensing apparatus capable of preferably suppressing the oscillation of the application voltage and also accurately detecting the gas concentration.

Preferably, an application voltage line is defined on the V-I coordinate for determining the voltage applied to the gas concentration sensor, and an inclination of the application voltage line is equalized to an inclination equivalent to the D.C. resistance of the gas concentration sensor element in a sensor activated condition. As described above, by reducing the change speed of the application voltage or setting the overall gain of the feedback circuit to be equal to or smaller than 1, and also by equalizing the inclination of the application voltage to the inclination equivalent to the element D.C. resistance, the gas concentration sensing apparatus is preferably applied to an air-fuel ratio control system for performing a lean burn control of an internal combustion engine so that a wide range of the air-fuel ratio can be detected.

Preferably, a plurality of application voltage lines different in their inclinations are set on the V-I coordinate to selectively or continuously use the plurality of application voltage lines in accordance with the temperature of the sensor element. Temperature change of the sensor element induces the shift of the limit-current sensing region shown in FIG. 3. However, providing the plurality of different application voltage lines makes it possible to select an optimum application voltage line in accordance with the momentary temperature of the sensor element. Thus, it becomes possible to prevent the gas concentration from being erroneous detected.

Hereinafter, preferred embodiments of the present invention will be explained in greater detail with reference to attached drawings. Identical parts are denoted by the same reference numerals throughout the views.

First Embodiment

The present invention can be embodied as an air-fuel ratio sensing apparatus. Thus, a first embodiment embodying such an air-fuel ratio sensing apparatus will be explained with reference to attached drawings.

The air-fuel ratio sensing apparatus of this embodiment can be incorporated into an electronically controlled gasoline injection engine installed in an automotive vehicle. In an air-fuel ratio control system of this engine, a fuel injection amount to be supplied to the engine is controlled based on the sensing result of the air-fuel ratio sensing apparatus so that the air-fuel ratio is equalized to a desirable value. According to this embodiment, the air-fuel ratio sensing apparatus is constituted by an analog circuit. This analog circuit controls an application voltage applied to a limit-current type A/F sensor. Furthermore, the analog circuit obtains air-fuel ratio information as well as element resistance information.

Figure 1:
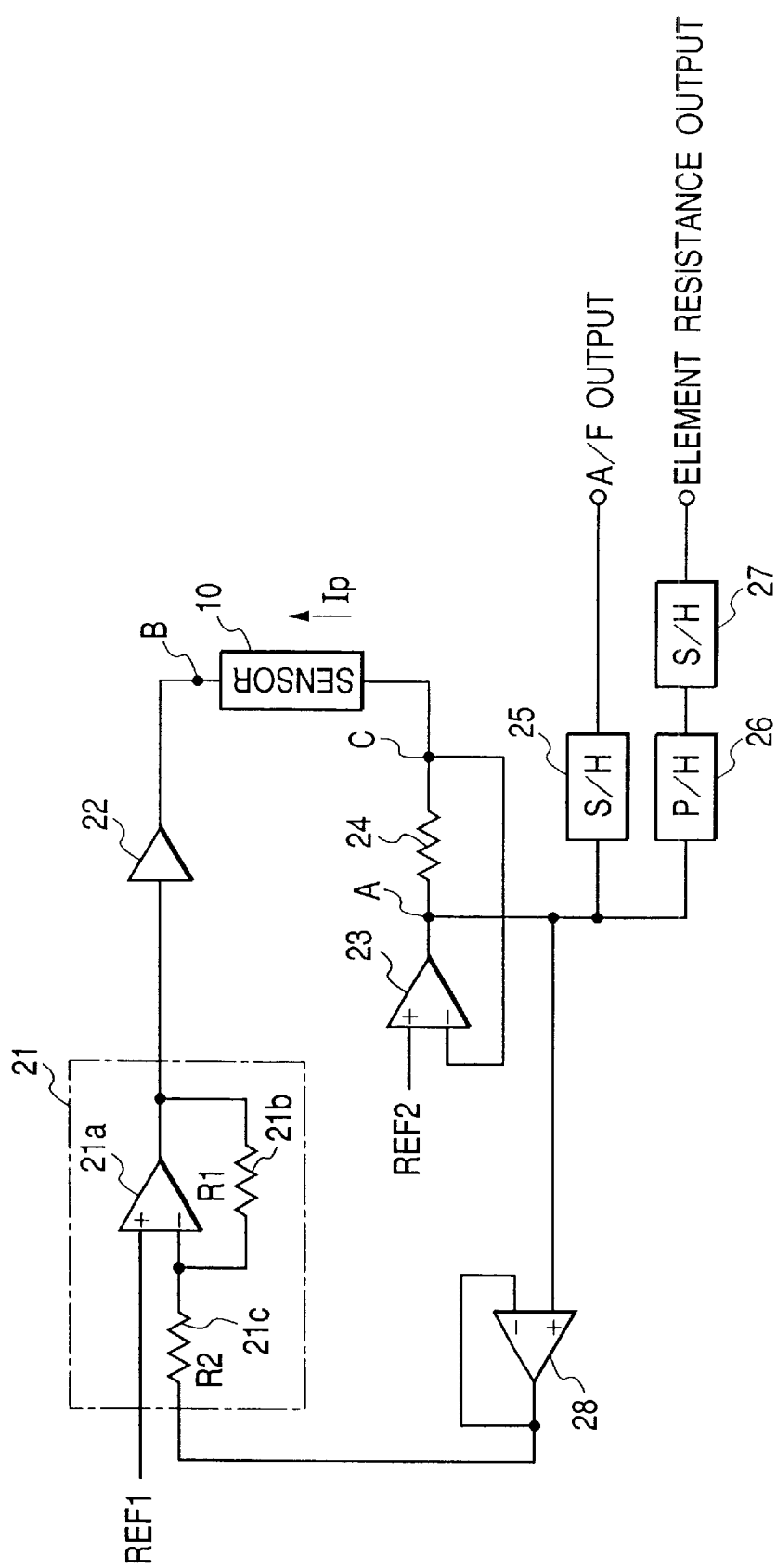
FIG. 1 is a circuit diagram showing a schematic arrangement of an air-fuel ratio sensing apparatus in accordance with a first embodiment of the present invention.

FIG. 1 is a circuit diagram showing a schematic arrangement of the air-fuel ratio sensing apparatus in accordance with first embodiment. In FIG. 1, an A/F sensor 10 has a sensor element portion 10a including a solid electrolytic member (refer to FIG. 2). The A/F sensor 10 detects an oxygen concentration in an exhaust gas emitted from the engine. Namely, the A/F sensor 10 produces a limit current (i.e., element current) which is responsive to the oxygen concentration in the exhaust gas in accordance with the application voltage applied to the sensor element portion 10a.

Figure 2:
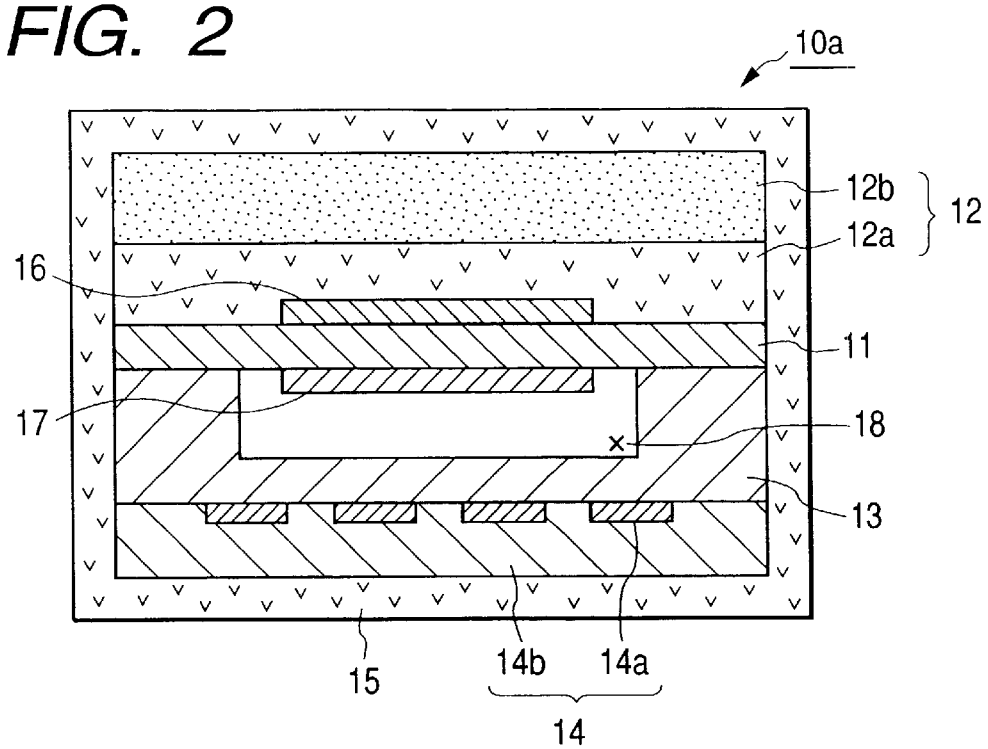
FIG. 2 is a cross-sectional view showing a detailed arrangement of a sensor element portion of an A/F sensor in the air-fuel ratio sensing apparatus shown in FIG. 1.

FIG. 2 shows a detailed arrangement of the sensor element portion 10a. The sensor element portion 10a is roughly constituted by a solid electrolytic member 11, a gas diffusive resistor layer 12, an air introducing duct 13, and a heater 14 which are laminated or stacked in a multilayered arrangement. All the multilayered members are surrounded by a protection layer 15.

The solid electrolytic member 11 is configured into an oblong plate and made of a partially-stabilized zirconia sheet. A measuring electrode 16, which is porous and made of platinum or the like, is provided on an upper surface of the solid electrolytic member 11 by screen printing. In other words, the measuring electrode 16 is provided on the surface of the solid electrolytic member 11 which is closer to the gas diffusive resistor layer 12. An atmospheric electrode 17, which is porous and made of platinum or the like, is provided on a lower upper surface of the solid electrolytic member 11 by screen printing. In other words, the atmospheric electrode 17 is provided on the opposite surface of the solid electrolytic member 11 which is closer to the air introducing duct 13.

The gas diffusive resistor layer 12 comprises a gas permeable layer 12a and a gas shielding layer 12b. The gas permeable layer 12a is made of a porous sheet and introduces the exhaust gas to the measuring electrode 16. The gas shielding layer 12b is made of a gas-tight sheet capable of suppressing the penetration of the exhaust gas. Each of the gas permeable layer 12a and the gas shielding layer 12b is manufactured from a ceramic material, such as alumina, spinel and zirconia, by using a sheet forming technique. The gas permeability of each layer 12a or 12b is differentiated by controlling an average pore size and a porosity.

The air introducing duct 13 is made of a high heat conductive ceramic material, such as alumina. An atmospheric chamber 18 is defined by the air introducing duct 13. The atmospheric electrode 17 is exposed to the air introduced into the atmospheric chamber 18 via the air introducing duct 13. The heater 14 is provided along the lower surface of the air introducing duct 13. The heater 14 comprises a plurality of heat generating elements 14a which generate heat in response to electric power supplied from a power battery. The heat generating elements 14a are covered by an insulating sheet 14b. However, the arrangement shown in FIG. 2 can be variously modified. For example, it is possible to embed each heat generating element 14a in the solid electrolytic member 11 or in the gas diffusive resistor layer 12.

According to the above-described arrangement of the sensor element portion 10a, the exhaust gas reaches the measuring electrode 16 without passing in the vertical direction (i.e., up-and-down direction in FIG. 2) of the gas permeable layer 12a. In other words, the exhaust gas enters from each lateral side of the gas permeable layer 12a. More specifically, as the surface of the gas permeable layer 12a is covered by the gas shielding layer 12b, the exhaust gas cannot flow in the vertical direction. Thus, the exhaust gas enters from the side surface of the gas permeable layer 12a and flows inside the gas permeable layer 12a in a direction normal to the vertical direction. In this case, the gas diffusion amount in the gas permeable layer 12a is dependent on the transverse (i.e., right-and-left directional) size of the gas permeable layer 12a. Actually, it depends on a distance between the side surface of the gas permeable layer 12a and the measuring electrode 16. This size can be easily and flexibly set. This makes it possible to stabilize the sensor output even if the pore size of the gas permeable layer 12a is not stable.

According to the above-described A/F sensor 10, the sensor element portion 10a produces limit current responsive to the oxygen concentration when the air-fuel ratio is shifted toward a lean region with respect to a theoretical (i.e., stoichiometric) air-fuel ratio. In this case, the sensor element portion 10a (i.e., solid electrolytic member 11) can use a linear characteristic in detecting the oxygen concentration. However, the sensor element portion 10a is not activated until the sensor temperature is increased up to approximately 600° C. Furthermore, due to a narrow activation temperature range of the sensor element portion 10a, it is difficult to maintain the activated condition by using only the exhaust gas of the engine. Accordingly, in this embodiment, the heater 14 (i.e., heat generating portion 14a) is controlled to maintain the temperature of the sensor element portion 10a in the activation temperature range. When the air-fuel ratio is shifted toward a rich region with respect to the theoretical air-fuel ratio, some concentration unburnt gases, such as carbon monoxide (CO), show a linear change in accordance with the air-fuel ratio. The sensor element portion 10a thus generates limit current responsive to the concentration of such unburnt gas.

FIG. 3 shows the V-I characteristics of the A/F sensor 10. In FIG. 3, the element current Ip (i.e., limit current) increases or decreases in response to the air-fuel ratio. The element current Ip increases as the air-fuel ratio shifts toward the lean side. On the other hand, the element current Ip decreases as the air-fuel ratio shifts toward the rich side. The voltage region extending from the straight-line portion (i.e., limit-current sensing region) to the lower voltage side is the resistance dominant region. In this resistance dominant region, the inclination of the first-order straight line portion is equivalent to the D.C. resistance Ri of the sensor element portion 10a (i.e., solid electrolytic member 11). This inclination varies in accordance with the element temperature. For example, the element D.C. resistance Ri increases with decreasing element temperature. The inclination becomes small. The element A.C. impedance Zac is regulated with respect to the element D.C. resistance Ri as shown in FIG. 3 (i.e., Ri>Zac).

As shown in FIG. 1, an application voltage control circuit 21 comprises an operational amplifier 21a and resistors 21b and 21c. The operational amplifier 21a has a non-inverting input terminal receiving a reference voltage REF1. The reference voltage REF1 is generally adjustable by an air-fuel ratio sensing application voltage. For example, the reference voltage REF1 is temporarily switched to an element resistance detecting application voltage every 128 msec. An output of the application voltage control circuit 21 is applied to one terminal of the A/F sensor 10 via a driver circuit 22.

The other terminal of the A/F sensor 10 is connected to an output terminal of an operational amplifier 23 via a current-detecting resistor 24. The operational amplifier 23 has a non-inverting input terminal receiving a reference voltage REF2. According to this embodiment, in order to use a single power source for this circuit, the reference voltage REF2 serves as a virtual ground. The current-detecting resistor 24 converts the element current flowing across the A/F sensor 10 into a voltage value. The converted voltage value representing the element current is supplied to a S/H (i.e., sample hold) circuit 25 and a P/H (i.e., peak hold) circuit 26.

The S/H circuit 25 samples the element current during the air-fuel ratio detecting operation, and successively updates the sample value and outputs the updated sample value in a predetermined gate-on period. An output of the S/H circuit 25 is a signal representing the detected air-fuel ratio and is, for example, sent to an engine control unit ECU (not shown). The air-fuel ratio feedback control can be thus performed based on this air-fuel ratio detecting value.

The P/H circuit 26 holds a peak value of the element current during a predetermined gate-on period corresponding to the element resistance detecting operation. The peak hold value of the P/H circuit 26 is sent to a S/H (i.e., sample hold) circuit 27. The S/H circuit 27 successively updates the sample value and outputs the updated sample value as a detection value of the element resistance. The detected element resistance value is, for example, sent to the engine control unit ECU. The engine control unit ECU can use the received element resistance value for various purposes, e.g., activation judgement, activation control, and diagnosis, relating to the A/F sensor 10. The peak hold value of the element current is reset in response to each gate-off operation.

The element current (i.e., the converted voltage value), detected by the current-detecting resistor 24, is returned to the application voltage control circuit 21 via a buffer 28. According to the apparatus shown in FIG. 1, the current flowing across the A/F sensor 10 varies in response to the air-fuel ratio. The application voltage is changed in accordance with the change of the detected current value. Through such a feedback control, the application voltage applied to the A/F sensor 19 is always controlled to an appropriate value.

During the element resistance detecting operation, the application voltage (i.e., reference voltage REFl) of the application voltage control circuit 21 is temporarily changed to a positive value and a negative value from the voltage value having being set for the preceding air-fuel ratio detecting operation. In this case, according to the frequency characteristics of the A/F sensor 10, the frequency of the application voltage for the element resistance detecting operation is set to 1 kHz or above. When seeking more stable characteristics, it is preferable to increase the frequency up to 3 kHz or above. By increasing the frequency, it becomes possible to shorten the detecting time of the element resistance. In other words, the dormant period of the air-fuel ratio detecting operation can be reduced.

Figure 10:
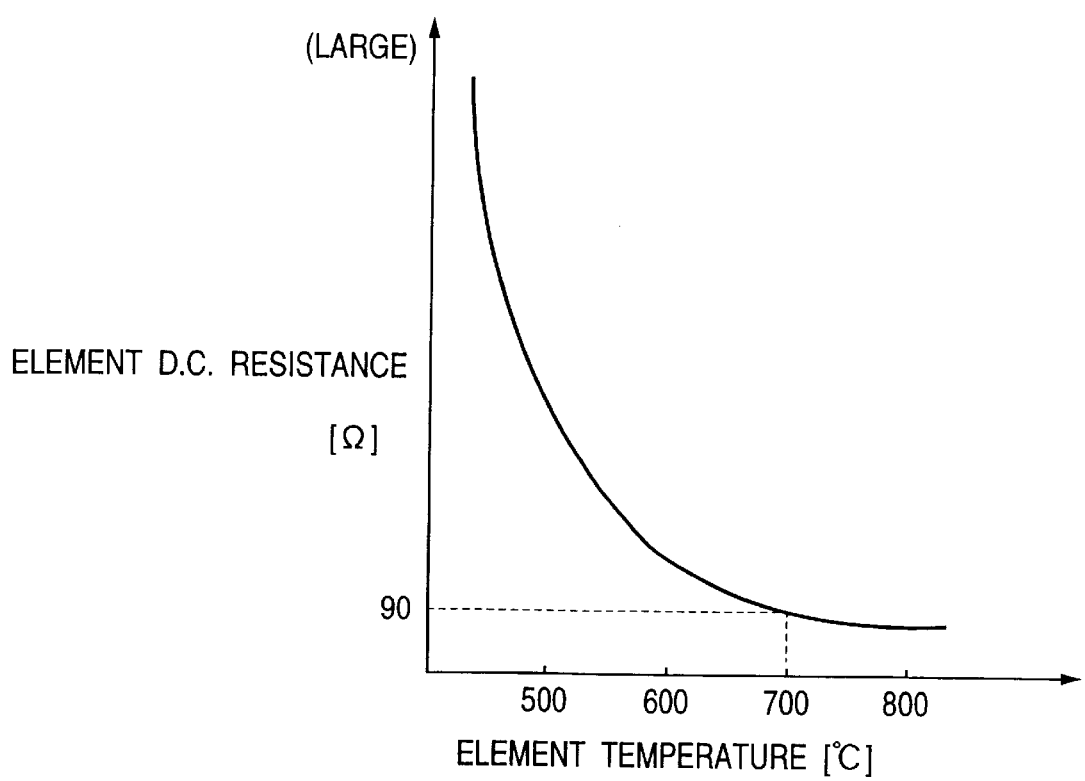
FIG. 10 is a graph showing a relationship between an element D.C. resistance and an element temperature.

The activation control of the A/F sensor 10 is performed in such a manner that the sensor element portion 10a is maintained at a predetermined activation temperature (e.g., 700° C.). FIG. 10 shows a relationship between the sensor temperature and the element resistance. A target element resistance for the designated activation temperature is given from the curve shown in FIG. 10. Thus, the element resistance is feedback controlled to the target value. For example, such a feedback control of the element resistance (i.e., element temperature) can be realized by controlling a duty ratio of electric power supplied to the heater 14.

Figure 4:
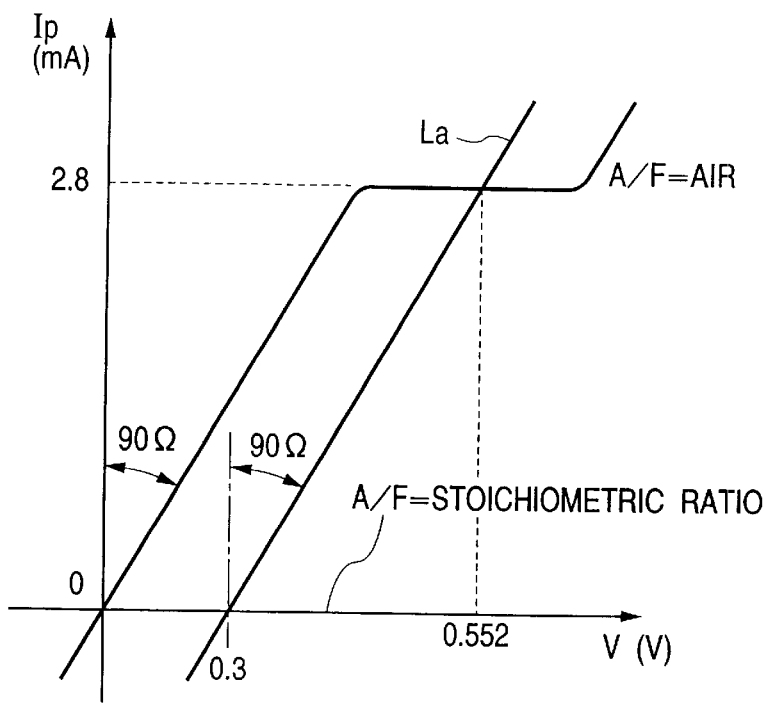
FIG. 4 is a graph showing an application voltage line on a V-I coordinate.

In this manner, the application voltage control circuit 21 varies the application voltage of the A/F sensor 10 in accordance with the detected element current (i.e., converted voltage value). However, when the overall gain of the feedback circuit shown in FIG. 1 exceeds "1", the application voltage causes oscillation. It is now assumed that the element D.C. resistance Ri is 90Ω at the sensor activated condition (i.e., at the element temperature 700° C.). Furthermore, as shown in FIG. 4, an application voltage line La is set to have an inclination parallel to that of the resistance dominant region. According to the application voltage line La of FIG. 4, "0.552V" is applied to the A/F sensor 10 when the air-fuel ratio is equivalent to the air. And, "0.3V" is applied to the A/F sensor 10 when the air-fuel ratio is equivalent to the stoichiometric air-fuel ratio.

Namely, the circuit parameters of the apparatus shown in FIG. 1 are determined in the following manner. The reference voltage REF2 is 3V (the voltage of a point "C" is also 3V). The resistance value of the current-detecting resistor 24 is 560Ω. The element current Ip is 2.8 mA for the air and 0 mA for the stoichiometric air-fuel ratio.

In this case, when the A/F ratio sensor 10 detects the air, the voltage value of the point "A" shown in FIG. 1 is given in the following manner.

$$3V + 2.8\ mA \times 560\Omega = 4.568V$$

The voltage value of the point "B" shown in FIG. 1 is given in the following manner.

$$3V - 0.552V = 2.448V$$

Similarly, when the A/F ratio sensor 10 detects the stoichiometric air-fuel ratio, the voltage value of the point "A" is given in the following manner.

$$3V + 0\ mA \times 560\Omega = 3V$$

The voltage value of the point "B" is given in the following manner.

$$2.7V = 3V - 0.3V$$

Accordingly, the gain β of the application voltage control circuit 21 is determined in the following manner.

$$\beta = \frac{Output}{Input} = \frac{2.448 - 2.7}{4.568 - 3} = -\frac{0.252}{1.568} \quad (4)$$

The gain β (0.252/1.568) is determined by the ratio (R1/R2) of the resistance values R1 and R2 of the resistors 21b and 21c.

Under the condition that the gain β is 0.252/1.568, the application voltage may change in response to generation of noise due to the A.C. characteristics of the A/F sensor 10. It is assumed that, when the element D.C. resistance Ri is 90Ω, the element A.C. impedance Zac is 80Ω.

Figure 5:
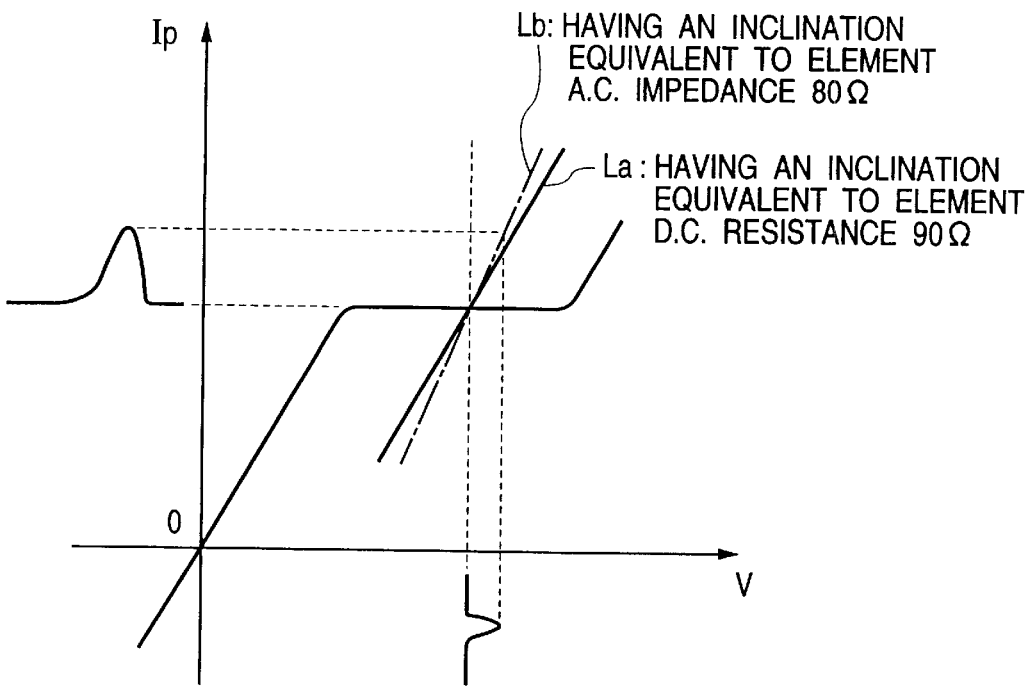
FIG. 5 is a graph showing application voltage lines on a V-I coordinate.

It is further assumed that the application voltage (i.e., the voltage at the point B in FIG. 1) showed a sudden change of "+0.1V" due to noise as shown in FIG. 5. The element current Ip changes by 1.25 mA (=0.1V/80Ω) according to the application voltage line Lb having the inclination equivalent to the element A.C. impedance. In this case, the voltage at the point A changes by 0.7V (=1.25 mA×560Ω). In response to this voltage change, the voltage at the point B (i.e., sensor application voltage) changes by 0.1125V (=0.7V×gain β). Accordingly, the sensor application voltage increases by 12.5 mV compared with the condition prior to the noise generation. Thus, the application voltage oscillates as a result of repetition of such voltage change.

On the other hand, in the feedback circuit constituted by the application voltage control circuit 21, A/F sensor 10 and current-detecting resistor 24, the gain of A/F sensor 10 based on the A.C. characteristics is expressed in the following manner.

$$\frac{Output}{Input} = \frac{Ip(mA)}{V(V)} = \frac{1}{R(\Omega)} = \frac{1}{80} \quad (5)$$

Furthermore, the gain of current-detecting resistor 24 is expressed in the following manner.

$$\frac{Output}{Input} = \frac{V(V)}{Ip(mA)} = R(\Omega) = 560 \quad (6)$$

Accordingly, the overall gain of the feedback circuit is given in the following manner.

$$\beta \times (1/80) \times 560 = 1.125$$

It is understood that the oscillation occurs as the overall gain exceeds 1.

As explained above, when the inclination of the resistance dominant region (i.e., element D.C. resistance Ri) is identical with the inclination of the application voltage line La on the V-I characteristics (refer to FIG. 4), the application voltage causes oscillation in response to the generation of noise.

When the application voltage is changed according to the D.C. characteristics of the A/F sensor 10, an overall gain of the feedback circuit is expressed in the following manner.

$$\beta \times (1/90) \times 560 = 1$$

It is understood that no oscillation phenomenon occurs when the application voltage varies in accordance with the element current Ip.

This embodiment uses an application voltage Lc having an inclination larger (i.e., steeper) than that of the application voltage Lb (equivalent to the element A.C. impedance Zac) shown in FIG. 6. Thus, the oscillation phenomenon caused by noises can be surely suppressed.

For example, the gain β of the application voltage control circuit 21 may be given in the following manner.

$$\beta = \frac{0.21}{1.568} \quad (7)$$

In this case, the overall gain of the feedback circuit based on the A.C. characteristics is expressed in the following manner.

$$\beta \times (1/80) \times 560 = 0.9338$$

Namely, as the overall gain is less than "1", it is understood that no oscillation occurs in response to occurrence of noise. In fact, to adjust the gain β in the above-described manner, the resistance values R1 and R2 of the resistors 21b and 21c are set to R1=1 kΩ and R2=7.5 kΩ in the application voltage control circuit 21.

As described above, the gain according to the A.C. characteristics of A/F sensor 10 is 1/80. The gain of the current-detecting resistor 24 is 560. Thus, to suppress the overall gain of the feedback circuit to value smaller than "1", the gain β needs to satisfy the following condition.

$$\beta > \frac{0.224}{1.568} \quad (8)$$

By satisfying this condition, the change rate of the application voltage produced by the application voltage control circuit 21 becomes smaller than the change rate corresponding to the A.C. characteristics of the A/C sensor 10. Thus, it becomes possible to suppress the oscillation phenomenon of the application voltage due to the sensor A.C. characteristics.

Furthermore, to obtain the desired sensor output characteristics (i.e., V-I characteristics), the A/F sensor 10 is maintained in a predetermined activation temperature region. However, the exhaust gas temperature increases when the engine is driven in a high speed or high load condition. The sensor element temperature increases in accordance with the exhaust gas temperature. The element resistance (i.e., element A.C. impedance Zac) decreases. When the element A.C. impedance Zac decreases, the gain of A/C sensor 10 increases. The application voltage tends to oscillate. Hence, according to this embodiment, increase of the exhaust gas temperature or the like is taken into consideration in determining the inclination of the application voltage. More specifically, the inclination of the application voltage line is determined under the specific condition where the A.C. impedance Zac is most lowest, i.e., under the condition where the element temperature is most highest.

The above-described first embodiment of the present invention has the following effects.

(a) In the application voltage control circuit 21, the inclination of the application voltage line on the V-I coordinate is set to be larger than the inclination equivalent to the element A.C. impedance Zac in the sensor activated condition. In this case, the overall gain of the feedback circuit including the application voltage control circuit 21 and the A/F sensor 10 is suppressed to a value smaller than 1. According to the above-described arrangement, it becomes possible to prevent the application voltage from being amplified by the application voltage control circuit 21 so excessively that it is brought into oscillated condition, even when the application voltage is changed suddenly due to power-on operation or occurrence of disturbance or the like. Hence, it becomes possible to effectively suppress the oscillation of the application voltage. The gas concentration can be accurately detected. Furthermore, by suppressing the oscillation of the application voltage, it becomes possible to prevent the A/F sensor 10 from being subjected to excessively large voltages for a long time. Thus, the sensor element is not damaged.

(b) Furthermore, the above-described embodiment makes it possible to suppress undesirable oscillation of the application voltage without using a microcomputer which is generally expensive. Using no microcomputer is effective to eliminate the tailing phenomenon caused in response to each change of the application voltage. In the element resistance detecting operation, the frequency of the application voltage is not restricted by the processing ability of each microcomputer. As the switching operation of the application voltage is performed at a high frequency, the dormant period of the air-fuel ratio detecting operation can be shortened. Such reduction of the dormant period leads to small dispersion in detected air-fuel ratio values in respective cylinders of the engine. In other words, the D/A or A/D converter and the microcomputer need not to have high-speed processing capability. This brings cost reduction and downsizing effects.

(c) Moreover, the above-described embodiment realizes an air-fuel ratio sensing apparatus using a multilayered A/F sensor (refer to FIG. 2) which has excellent warmup ability even in an engine cold startup condition. Accordingly, the sensor element 10a is promptly warmed up. For example, it takes only several seconds until the application voltage line Lc shown in FIG. 6 becomes usable. In this case, it is not necessary to provide a plurality of application voltage lines. The application voltage control for the A/F sensor 10 can be performed by using the application voltage line Lc only.

Next, second and third embodiments of the present invention will be explained. In each embodiment, parts or components substantially identical with those disclosed in the first embodiment are denoted by the same reference numerals and not explained in detail. Hereinafter, difference between the second or third embodiment and the above-described first embodiment will be chiefly explained.

Second Embodiment

Figure 7:
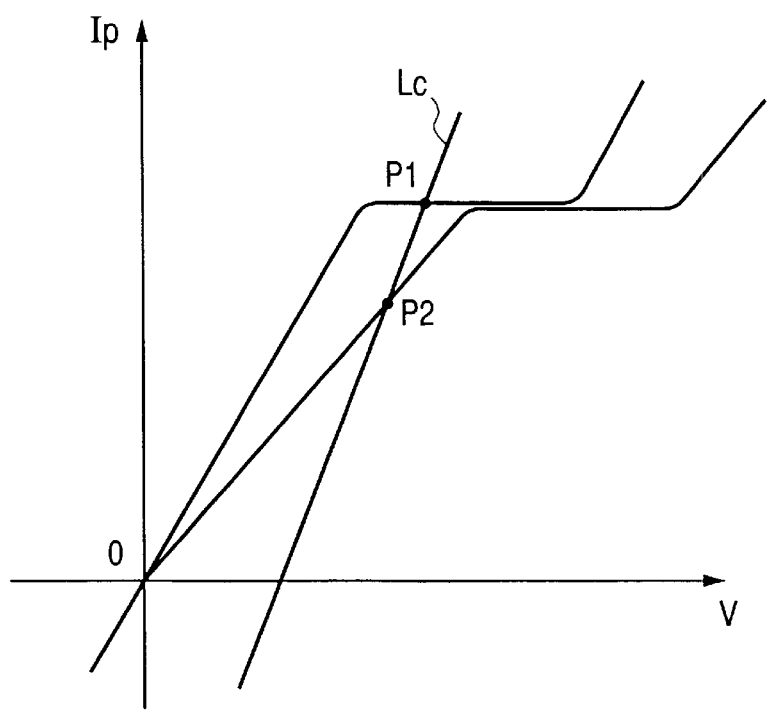
FIG. 7 is a graph showing an application voltage line on a V-I coordinate.

According to the above-described first embodiment, the inclination of the application voltage line is determined based on the most-lowest A.C. impedance Zac (i.e., most-highest element temperature) so that the oscillation of application voltage can be suppressed even in the high-speed and high-load conditions. However, when the sensor element temperature decreases in response to reduction of the exhaust gas temperature, the element resistance increases according to the relationship shown in FIG. 10. In this case, the application voltage line may not cross the limit-current sensing region (i.e., straight-line portion parallel to the V-axis) as shown in FIG. 7. The sensing accuracy in the air-fuel ratio detecting operation will be worsened. More specifically, when the application voltage line Lc crosses the limit-current sensing region at the point P1 of FIG. 7, the element current Ip corresponding to the point P1 correctly represents the air-fuel ratio. However, when the application voltage line Lc crosses the resistance dominant region at the point P2 of FIG. 7, the element current Ip corresponding to the point P2 erroneously represents the air-fuel ratio.

Figure 8:
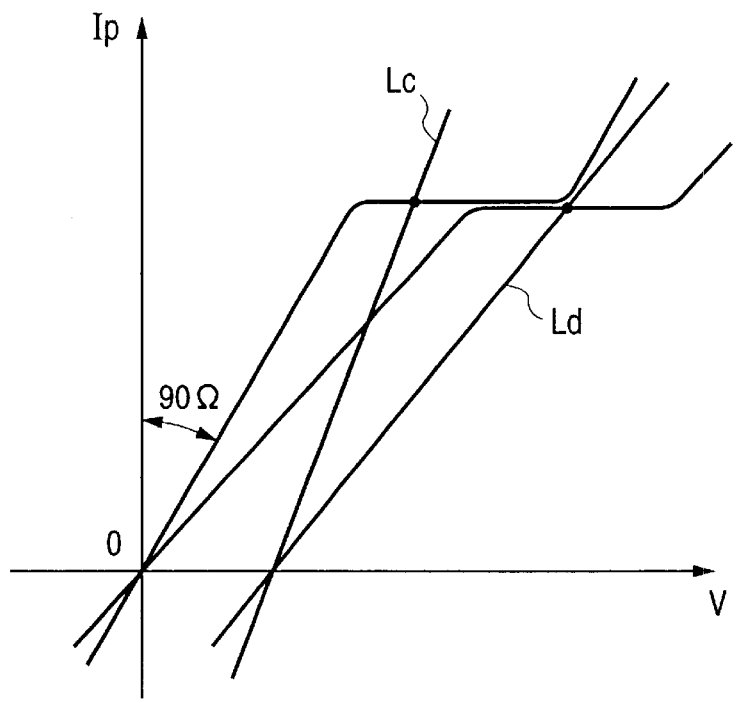
FIG. 8 is a graph showing application voltage lines on a V-I coordinate.

Hence, according to the second embodiment, as shown in FIG. 8, another application voltage line Ld is provided in addition to the application voltage line Lc determined based on the above-described high-temperature condition. Two application voltage lines Lc and Ld are selectively used in accordance with element temperature information which is momentarily obtained.

Figure 9:
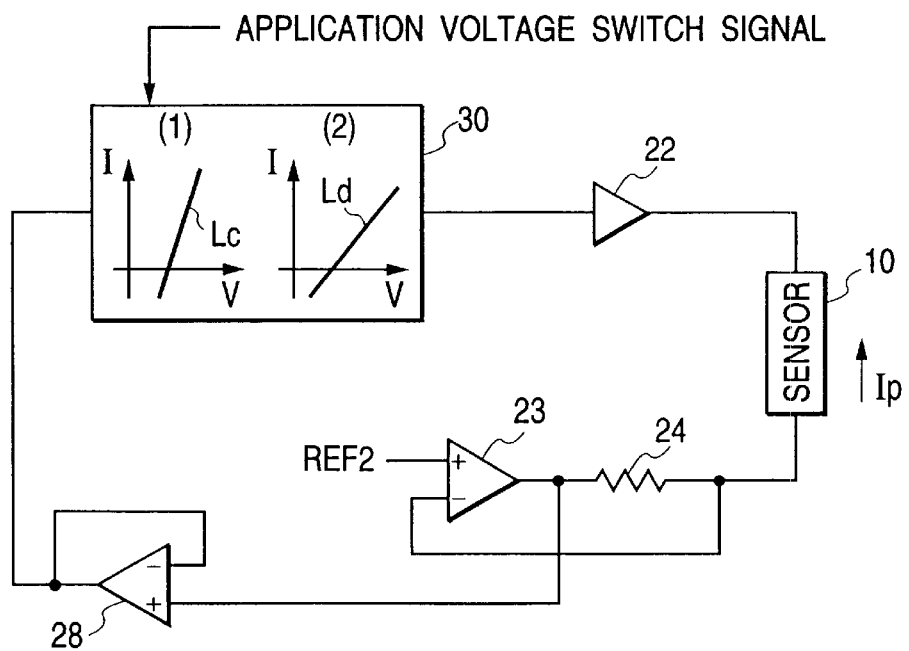
FIG. 9 is a circuit diagram showing a schematic arrangement of an air-fuel ratio sensing apparatus in accordance with a second embodiment of the present invention.

FIG. 9 is a schematic circuit diagram showing an arrangement of an air-fuel ratio sensing apparatus in accordance with the second embodiment. An application voltage control circuit 30 selects one of two application voltage lines Lc and Ld. For example:

(1) One application voltage line Lc has an inclination larger or steeper than the inclination equivalent to the A.C. impedance Zac at a predetermined high-temperature condition (e.g., element temperature= approximately 800° C.); and (2) The other application voltage line Ld has an inclination larger or steeper than the inclination equivalent to the A.C. impedance Zac at a reduced-temperature condition (e.g., element temperature=approximately 600° C.).

The application voltage control circuit 30 controls the application voltage in accordance with the selected application voltage line. An application voltage switch signal is produced based on the element temperature information. Selection between application voltage lines Lc and Ld is performed with reference to the application voltage switch signal.

Accordingly, when the engine is operated in the high-speed and high-load conditions, the gain of the application voltage control circuit 30 is adjusted so as to correspond to the application voltage line Lc. In this case, the application voltage is controlled in accordance with the application voltage line Lc so that the oscillation of the application voltage is surely suppressed in the high-speed and high-load conditions. Furthermore, when the sensor temperature is lowered, the gain of the application voltage control circuit 30 is changed so as to correspond to the other application voltage line Ld. The application voltage is thus controlled in accordance with the application voltage line Ld so that the oscillation of the application voltage is surely suppressed in the lower-temperature conditions.

As apparent from the foregoing description, the above-described second embodiment brings the following effects in addition to the effects of the above-described first embodiment. Namely, a plurality of application voltage lines having different inclinations are provided on the V-I coordinate. One of these plurality of application voltage lines is selected in accordance with the sensor element temperature. Thus, it becomes possible to accurately detect the air-fuel ratio even when the sensor element temperature is decreased unexpectedly.

Third Embodiment

Figure 11:
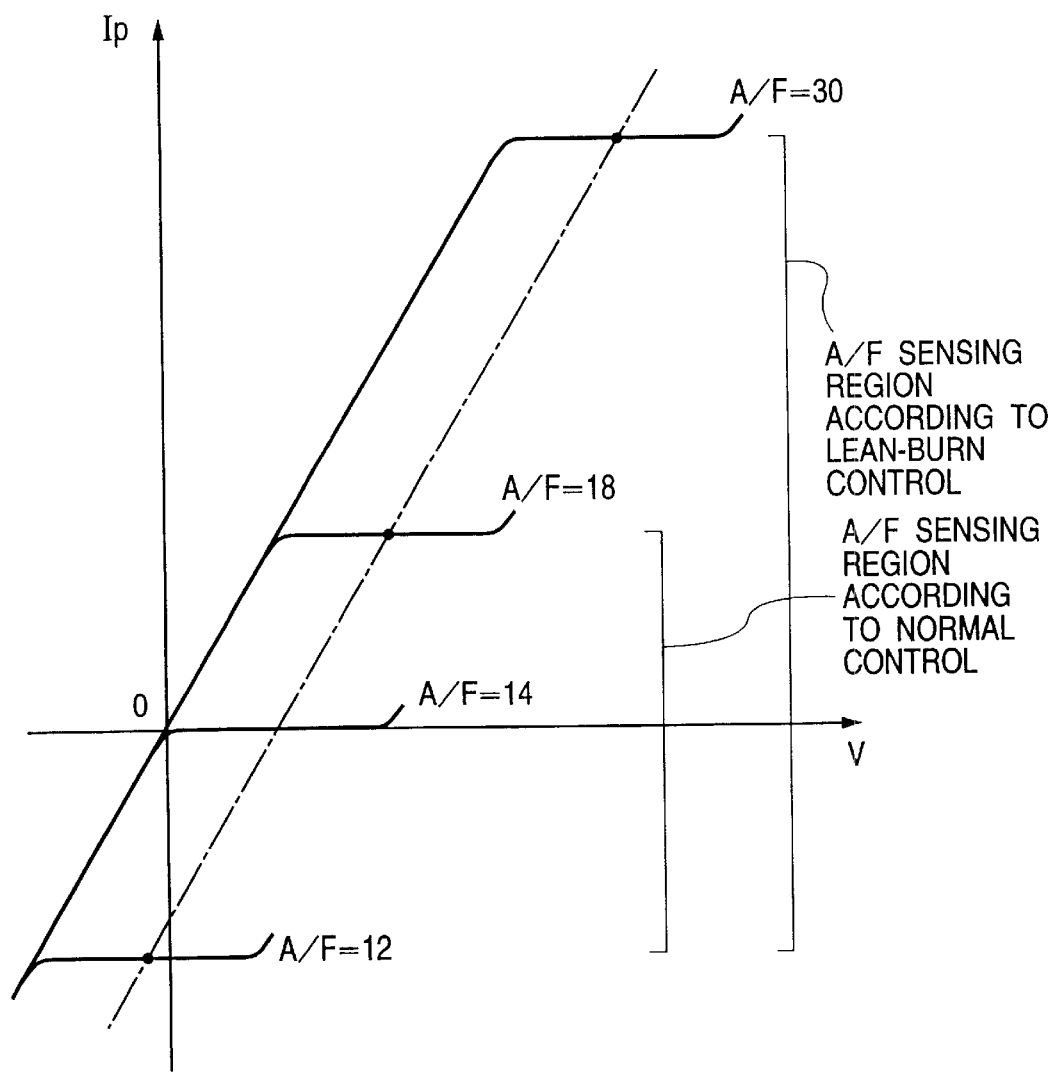
FIG. 11 is a graph showing an application voltage line on a V-I coordinate.

When the air-fuel ratio control is performed in the vicinity of the stoichiometric air-fuel ratio, an air-fuel ratio sensing region generally ranges from 12 to 18. On the other hand, when the lean burn control is performed to adjust the air-fuel ratio to a lean side, the air-fuel ratio sensing region extends adjacent to 30 as shown in FIG. 11. Hence, when the inclination of the application voltage line is larger or steeper than the inclination of the resistance dominant region, the application voltage may not cross the limit-current sensing region. The sensing accuracy of the air-fuel ratio is worsened.

According to the third embodiment of the present invention, like the application voltage line L1 shown in FIG. 3, the inclination of the application voltage line is equalized with that of the resistance dominant region on the V-I characteristics so that the application voltage line always crosses the limit current sensing region. Furthermore, a LPF (i.e., low-pass filter) is incorporated in the air-fuel ratio sensing apparatus to suppress the oscillation of the application voltage.

Figure 12:
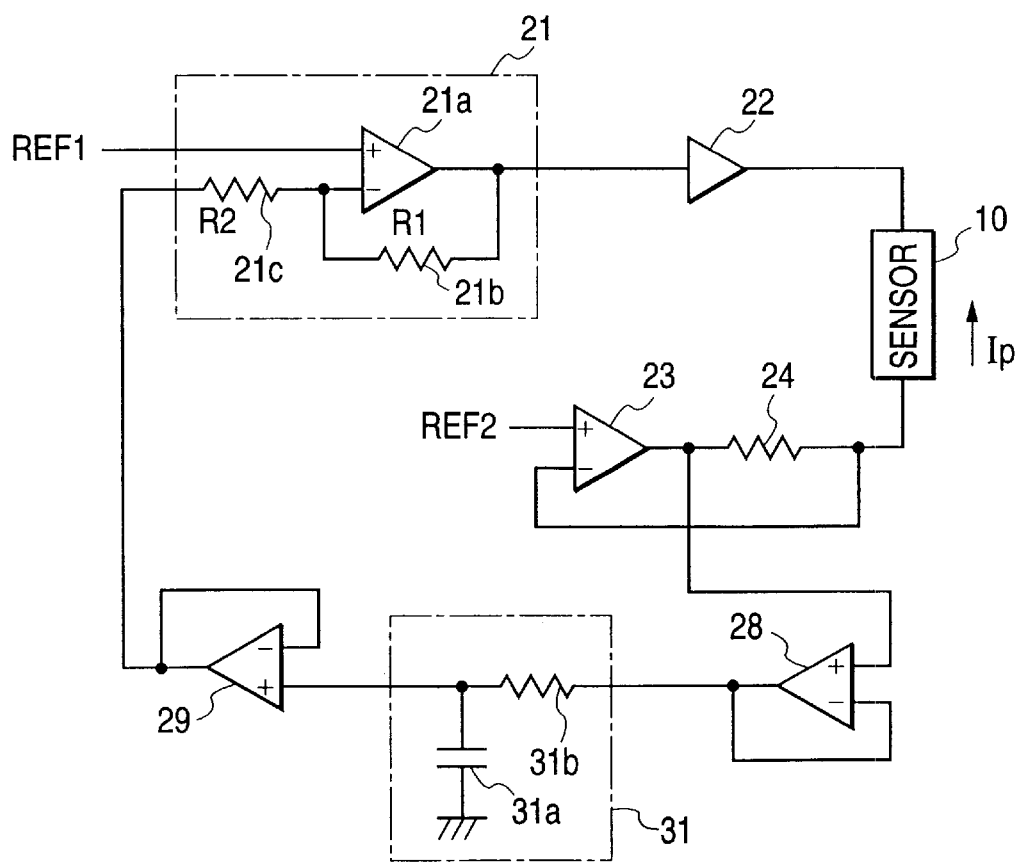
FIG. 12 is a circuit diagram showing a schematic arrangement of an air-fuel ratio sensing apparatus in accordance with a third embodiment of the present invention.

FIG. 12 is a schematic circuit diagram showing an arrangement of an air-fuel ratio sensing apparatus in accordance with the third embodiment. In FIG. 12, an element current value detected by the current-detecting resistor 24 is supplied via a buffer 28 to a first-order LPF 31 consisting of a capacitor 31a and a resistor 31b. The LPF 31 removes high-frequency components of the element current. After being processed in the LPF 31, the element current is returned via a buffer 29 to the application voltage control circuit 21. The LPF 31 is not limited to a first-order LPF and therefore can be replaced by a second-order or third-order LPF. Furthermore, the LPF 31 can be provided anywhere in the feedback circuit including the application voltage control circuit 21 and the A/F sensor 10. For example, it is possible to provide the LPF 31 at an output side of the application voltage control circuit 21.

Figure 13B:
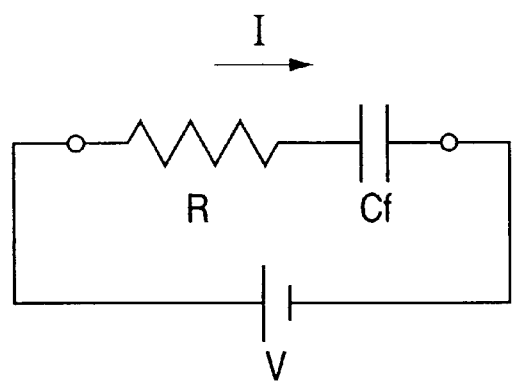
FIG. 13B is a view showing an equivalent circuit of the A/F sensor.
Figure 13C:
FIG. 13C is a view showing a model of a simple HPF realizing the equivalent circuit shown in FIG. 13B.

FIG. 13A shows an equivalent circuit of the limit-current type A/F sensor 10 using the solid electrolytic member. In FIG. 13A, Rg represents a particle resistance of the solid electrolytic element relative to the oxygen ion. Ri and Ci represent a particle resistance and an intergranular capacitance at a particle surface of the solid electrolytic member, respectively. Rf and Cf represent an electrode surface resistance and an electrode surface capacitance, respectively. In a practical circuit, the rising of the actual voltage applied to the A/F sensor 10 is in a level of several to several tens kHz. Almost all of the current flows across the path of Rg-Ri-Cf. Hence, the equivalent circuit shown in FIG. 13A can be modified into a simple circuit shown in FIG. 13B. Furthermore, FIG. 13C shows a model of a simple HPF (i.e., high-pass filter) realizing the equivalent circuit shown in FIG. 13B.

Figure 14A:
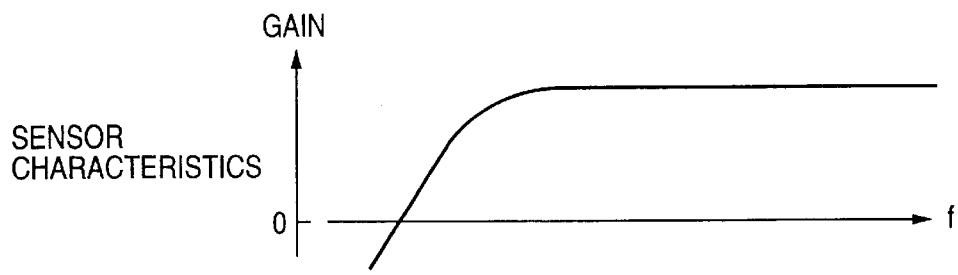
FIG. 14A is a graph showing frequency characteristic of the A/F sensor.
Figure 14B:
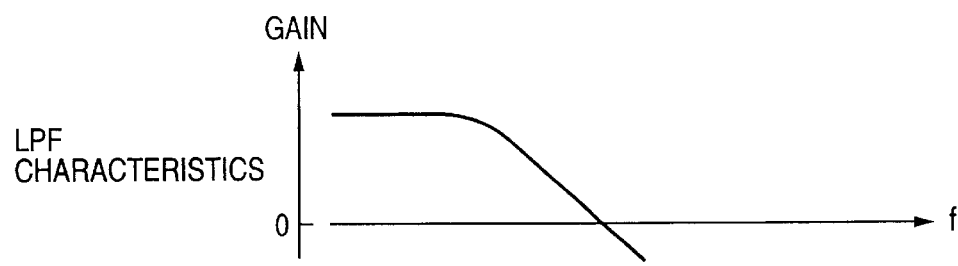
FIG. 14B is a graph showing frequency characteristic of an LPF.
Figure 14C:
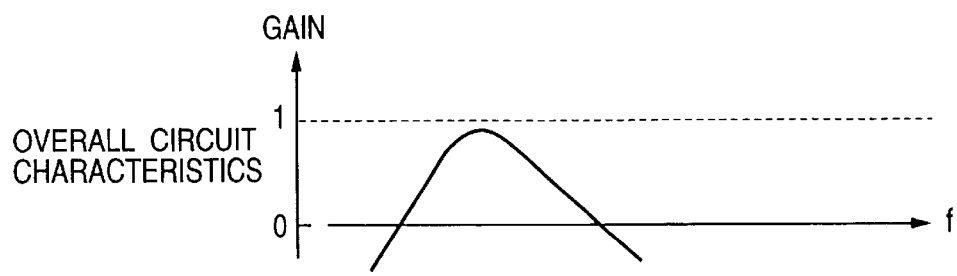
FIG. 14C is a graph showing overall frequency characteristic of the circuit.

In this case, the frequency characteristics of the A/F sensor 10 is shown in FIG. 14A. The frequency characteristics of the LPF 31 is shown in FIG. 14B. Accordingly, the overall frequency characteristics of the circuit is shown in FIG. 14C. The gain is smaller than 1 in the entire frequency range. Thus, it becomes possible to suppress the oscillation of the application voltage.

When the LPF 31 is incorporated in the circuit, the sensor response is significantly worsened. Thus, it is necessary to determine the time constant by considering such deterioration of sensor response together with the suppression of the oscillation. Furthermore, in determining the time constant, it is desirable to take unevenness of the sensor and its parts into consideration. According to this embodiment, the time constant of LPF 31 is set to approximately 10 Hz.

As described above, according to the third embodiment, the LPF 31 is incorporated into the air-fuel ratio sensing apparatus to reduce the change speed of the application voltage in the application voltage control circuit 21. Thus, the sudden voltage change occurring due to noise or the like can be moderated or absorbed by the LPF 31. It becomes possible to suppress the application voltage from oscillating. Furthermore, the sensing accuracy in the air-fuel ratio detecting operation can be maintained at an adequate level.

Furthermore, the inclination of the application voltage line on the V-I coordinate is equalized with the inclination equivalent to the element D.C. resistance Ri of the A/F sensor 10 in the sensor activated condition. With this setting, it becomes possible to adequately detect the air-fuel ratio in a wide range. Thus, this embodiment is preferably applied to the air-fuel ratio control system for performing the lean burn control.

The present invention can be embodied in various ways. For example, the following arrangements can be used for suppressing the overall gain of the feedback circuit to a value less than 1, and for reducing the change speed of the application voltage produced by the application voltage control circuit in accordance with the current signal.

(a) The change speed of the application voltage produced by the application voltage control circuit 21 is reduced in such a manner that a resistance value obtainable by the application voltage per unit time is smaller than the A.C. impedance Zac of the sensor element portion 10a. For example, a delay circuit is added in the feedback system as shown in FIG. 21A. With this arrangement, it becomes possible to limit the transitional element current (A.C. current component) detectable by a shunt resistor (serving as the current-detecting resistor 24). The application voltage change is relatively small compared with a large current change. Thus, the application voltage line becomes steep.

(b) As a means for reducing the change speed of the application voltage produced by the application voltage control circuit 21, it is preferable that the operational amplifier 21a in the application voltage control circuit 21 has a slow slew rate. For example, the slew rate of the operational amplifier 21a is delayed so that the resistance value obtainable by the application voltage per unit time becomes smaller than the A.C. impedance Zac of the sensor element.

(c) The LPF 31 shown in FIG. 12 can be replaced by an integrating circuit.

Figure 15A:
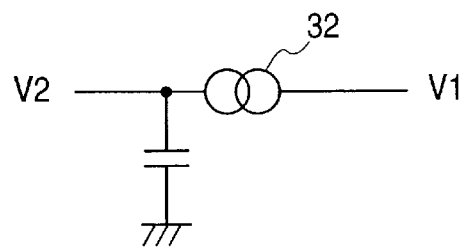
FIG. 15A is a view showing a circuit arrangement for reducing the change speed of the application voltage.
Figure 15B:
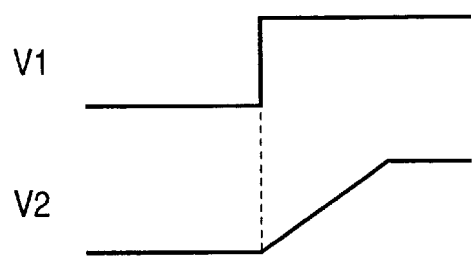
FIG. 15B is a time chart showing voltage changes.
Figure 16:
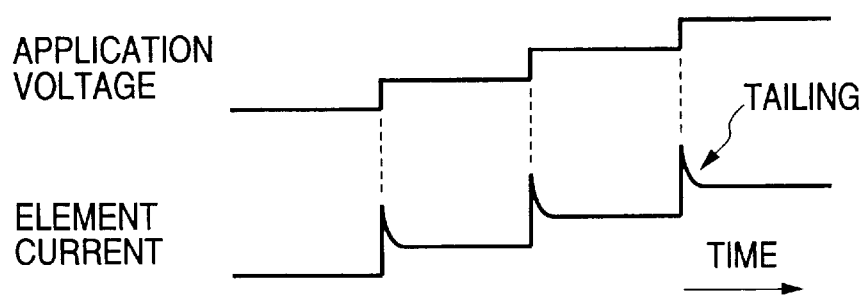
FIG. 16 is a view showing changes of the application voltage and an element current in accordance with the a conventional microcomputer-based gas concentration detecting apparatus.

(d) The LPF 31 shown in FIG. 12 can be replaced by a circuit shown in FIG. 15A. The circuit shown in FIG. 15A uses a constant-current circuit 32 instead of using the resistor 31a of th LPF 31. FIG. 15B shows the change (V1→V2) of the application voltage obtained by providing the circuit shown in FIG. 15A. As apparent from FIG. 15B, the change speed of the application voltage can be reduced adequately. In any of the above-described (a) through (d) cases, the purpose of the present invention can be attained. Namely, the oscillation of the application voltage can be adequately suppressed.

According to the above-described second embodiment, a plurality of application voltage lines are selectively used. However, this arrangement can be modified in the following manner.

It is preferable to momentarily vary the gain of the application voltage control circuit in accordance with the sensor element temperature (element resistance) so that the inclination of the application voltage line can be continuously changed. For example, the resistor 21c shown in FIG. 1 can be replaced by a variable resistor having a resistance value changeable in accordance with the sensor element temperature (element resistor).

In the above-described first to third embodiments, it is preferable to provide another application voltage line applicable to a low-temperature condition so that the application voltage for the A/F sensor can be controlled even in a transient state reaching the activated condition from the cold condition. In this case, it is preferable to provide a plurality of application voltage lines including the additionally provided application voltage line for the low-temperature condition. It becomes possible to appropriately control the application voltage in every temperature region.

Each of the above-described embodiments can be embodied as an air-fuel ratio sensing apparatus using a cup-shaped air-fuel ratio sensor in the same manner as in the air-fuel ratio sensing apparatus using the multilayered air-fuel ratio sensor. Furthermore, the present invention can be applied to other gas concentration sensing apparatuses using another type gas concentration sensors which detect NOx, HC, CO or the like. In such other gas concentration sensing apparatuses, the oscillation of the application voltage can be suppressed and the gas concentration can be accurately detected by using the techniques disclosed in the above-described embodiments.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas concentration sensing apparatus comprising:
    a sensor element including a solid electrolytic member with electrodes provided on opposite surfaces of said solid electrolytic member;
    a gas concentration sensor for generating a current signal (I) responsive to a concentration of a specific component involved in a measured gas when an application voltage (V) is applied between said electrodes of said sensor element; and
    an analog feedback control circuit including said sensor element therewithin for feedback controlling the application voltage applied to said gas concentration sensor in response to said current signal according to an application voltage versus current line having a change in voltage versus a change in current ($\Delta V/\Delta I$) inclination on V-I characteristic curves for said sensor;
    wherein said inclination is set to be smaller than an alternating current impedance (Zac) of said sensor element measured at 1 kHz or above at a maximum operating temperature of said sensor element, whereby oscillation of said application voltage in said feedback control circuit is suppressed at all times including even high operating temperature conditions.

2. The gas concentration sensing apparatus as in claim 1 wherein the analog feedback control circuit is configured such that the inclination of said line is larger than the inclination of the alternating current impedance of said sensor element when said sensor element is in a sensor-activated condition.

3. The gas concentration sensing apparatus as in claim 2 wherein said application voltage control circuit is configured to control the application voltage applied to said gas concentration sensor according to one of a plurality of application voltage lines, the plurality of application voltage lines being different in their inclinations, the one application voltage line according to which the application voltage control circuit controls the application voltage at a given time being determined in accordance with the temperature of the sensor element.

4. A gas concentration sensing apparatus comprising:
    a sensor element including a solid electrolytic member with electrodes provided on opposite surfaces of said solid electrolytic member;
    a gas concentration sensor which generates a current signal responsive to a concentration of a specific component in a measured gas when an application voltage is applied between said electrodes;
    an analog feedback control circuit including said sensor element therewithin for feedback controlling said application voltage applied to said gas concentration sensor in response to said current signal; and
    means for suppressing the time rate at which the application voltage changes in response to a change in said current signal during a transitional state of said current signal,
    said suppressing means being provided in a feedback loop of said feedback control circuit so that said time rate when expressed as a change in voltage versus a change in current ($\Delta V/\Delta I$) or as a resistance is always smaller than an alternating current impedance of said sensor element at all times including even during said transition state of the current signal whereby oscillation of said application voltage in said feedback control circuit is suppressed.

5. The gas concentration sensing apparatus as in claim 4 wherein said means for suppressing a low-pass filter.

6. The gas concentration sensing apparatus as in claim 4 wherein said means for suppressing comprises an operational amplifier included as a component of said analog feedback control circuit to adjust said time rate.

7. The gas concentration sensing apparatus as in claim 4 wherein the analog feedback control circuit is configured such that the inclination of said application voltage line is equal to the inclination of the direct current resistance of the sensor element of said gas concentration sensor when said sensor element is in a sensor-activated condition.

8. The gas concentration sensing apparatus as in claim 7 wherein said gas concentration sensing apparatus is incorporated in an air-fuel ratio control system for performing lean burn control of an internal combustion engine.

9. The gas concentration sensing apparatus as in claim 7 wherein said analog feedback control circuitry is configured to control the application voltage applied to said gas concentration sensor according to one of a plurality of application voltage lines, the plurality of application voltage lines being different in their inclinations the one application voltage line according to which the analog feedback control circuit controls the application voltage being determined in accordance with the temperature of the sensor element.

10. A gas concentration sensing apparatus comprising:
- a sensor element including a solid electrolytic member with electrodes provided on opposite surfaces of said solid electrolytic member;
- a gas concentration sensor for generating a current signal responsive to a concentration of a specific component involved in a measured gas when an application voltage is applied between said electrodes of said sensor element;
- an application voltage control circuit for feedback controlling said application voltage applied to said gas concentration sensor in response to said current signal; and
- means for suppressing the time rate at which the application voltage changes in response to a change in said current signal during a transitional state of said current signal, said suppressing means being provided in a feedback loop of said application voltage control circuit so that said time rate when converted into resistance is always smaller than an alternating current impedance of said sensor element during said transitional state of the current signal,
- wherein said means for suppressing comprises a low-pass filter which satisfies the condition $RG<(1+T_L/T)$ Zac where RG represents said time rate expressed in terms of resistance, $T_L$ represents a time constant of said low-pass filter, T represents a time constant of said gas concentration sensor, and Zac represents said alternating current impedance of said sensor element.

11. The gas concentration sensing apparatus as in claim 10 wherein said means for suppressing is configured such that a rate of change of the application voltage with respect to a rate of change of said current signal ($\Delta V/\Delta I$) is always smaller than said alternating current impedance of the sensor element during said transitional state.

12. The gas concentration sensing apparatus as in claim 10 wherein said means for suppressing comprises an operational amplifier included as a component of said application voltage control circuit to adjust said time rate.

13. The gas concentration sensing apparatus as in claim 10 wherein the application voltage control circuit is configured such that when an application voltage line for determining the voltage to be applied to said gas concentration sensor is defined on a V-I coordinate system, with the abscissa of said V-I coordinate system representing application voltage and the ordinate of said V-I coordinate system representing current signal, the inclination of said application voltage line relative to the abscissa of said V-I coordinate system in equal to the inclination equivalent, relative to the abscissa of said V-I coordinate system, of the direct current resistance of the sensor element of said gas concentration sensor when said sensor element is in a sensor-activated condition.

14. The gas concentration sensing apparatus as in claim 13 wherein said application voltage control circuitry is configured to control the application voltage applied to said gas concentration sensor according to one of a plurality of application voltage lines, the plurality of application voltage lines being different in their inclinations relative to said abscissa, the one application voltage line according to which the application voltage control circuit controls the application voltage at a given time being determined in accordance with the temperature of the sensor element.

15. The gas concentration sensing apparatus as in claim 10 wherein said gas concentration sensing apparatus is incorporated in an air-fuel ratio control system for performing lean burn control of an internal combustion engine.

* * * * *